US008063261B2

(12) United States Patent
Rokicki et al.

(10) Patent No.: US 8,063,261 B2
(45) Date of Patent: Nov. 22, 2011

(54) MULTI-LAYERED DEHYDROGENATION CATALYST SYSTEM AND PROCESS OF USE

(75) Inventors: Andrzej Rokicki, Mountain Lakes, NJ (US); Vladimir Fridman, Louisville, KY (US); Michael Urbancic, Louisville, KY (US)

(73) Assignee: Sud-Chemie Inc., Louisville, KY (US)

( * ) Notice: Subject to any disclaimer, the term of this patent is extended or adjusted under 35 U.S.C. 154(b) by 1078 days.

(21) Appl. No.: 11/129,834

(22) Filed: May 16, 2005

(65) Prior Publication Data

US 2006/0149112 A1 Jul. 6, 2006

Related U.S. Application Data

(60) Continuation-in-part of application No. 10/968,456, filed on Oct. 19, 2004, which is a division of application No. 10/047,598, filed on Jan. 14, 2002, now abandoned.

(51) Int. Cl.
*B01J 23/26* (2006.01)
(52) U.S. Cl. ...................................... 585/663; 502/320
(58) Field of Classification Search .................. 585/663; 502/320
See application file for complete search history.

(56) References Cited

U.S. PATENT DOCUMENTS

| | | | |
|---|---|---|---|
| 2,300,971 A | 11/1942 | Roberts | |
| 2,374,404 A | 4/1945 | Ahlberg | |
| 2,375,402 A | 5/1945 | Corson | |
| 2,399,678 A | 5/1946 | Houdry | |
| 2,423,029 A | 6/1947 | Houdry | |
| 2,943,067 A | 6/1960 | Sieg | |
| 2,945,823 A | 7/1960 | Cornelius | |
| 2,956,030 A | 10/1960 | Cornelius | |
| 2,973,330 A * | 2/1961 | Kant et al. | 502/334 |
| 2,985,596 A | 5/1961 | Pitzer | |
| 3,202,725 A * | 8/1965 | Waldemar et al. | 585/315 |
| 3,322,849 A | 5/1967 | McEuen | |
| 3,363,023 A | 1/1968 | Mooi | |
| 3,488,402 A | 1/1970 | Michaels | |
| 3,719,721 A | 3/1973 | Hansford | |
| 3,801,672 A | 4/1974 | Bajars | |
| 3,945,946 A | 3/1976 | Hindin | |
| 3,976,034 A | 8/1976 | Shinohara | |
| 4,716,143 A | 12/1987 | Imai | |
| 4,746,643 A | 5/1988 | Buonomo | |
| 4,786,625 A | 11/1988 | Imai | |
| 4,880,764 A | 11/1989 | Imai | |
| 5,378,350 A | 1/1995 | Zimmerman | |
| 5,510,557 A | 4/1996 | Gartside | |
| 6,124,228 A * | 9/2000 | Wu et al. | 502/64 |
| 6,417,422 B1 | 7/2002 | Liu | |

FOREIGN PATENT DOCUMENTS

| | | |
|---|---|---|
| EP | 0947247 | 10/1999 |
| GB | 942944 | 11/1963 |
| GB | 1424382 | 2/1976 |
| WO | WO0188244 | 3/2001 |
| WO | WO2005040075 A1 | 5/2005 |

OTHER PUBLICATIONS

Oberlander, Richard K., "Aluminas for Catalysts—Their Preparation and Properties", Applied Industrial Catalysis, vol. 3 (1983), p. 69.
Richardson, James T., "Principles of Catalyst Development", Fundamental and Applied Catalysis (1989), pp. 35-36.
Tsuchida, Takeshi, et al., "The effect of $Cr^{3+}$ and $Fe^{3+}$ ions on the transformation of different aluminum hydroxide to alpha-$Al_2O_3$", Thermochimica Acta, 64 (1983), pp. 337-353.
Office Action dated Nov. 9, 2007 with respect to U.S. Appl. No. 10/968,456.
Office Action dated Aug. 7, 2003 with respect to U.S. Appl. No. 10/047,598.
Office Action dated Mar. 22, 2004 with respect to U.S. Appl. No. 10/047,598.
Final Office Action dated Jul. 20, 2004 with respect to U.S. Appl. No. 10/047,598.
Advisory Action dated Sep. 30, 2004 with respect to U.S. Appl. No. 10/047,598.
Office Action dated Jun. 5, 2008 with respect to U.S. Appl. No. 10/968,456.
Rokicki, Andrzej, Catalyst in Petroleum Refining and Petrochemicals, Proceeding of the Saudi-Japanese Symposium, 11th, Dhahran, Saudi Arabia, Nov. 11-12, 2001.
Response filed Mar. 6, 2009 to Notice dated Feb. 10, 2009 regarding U.S. Appl. No. 10/968,456.
Final Office Action dated Oct. 8, 2008 with respect to U.S. Appl. No. 10/968,456.

\* cited by examiner

*Primary Examiner* — Stuart Hendrickson
(74) *Attorney, Agent, or Firm* — McDonnell, Boehnen Hulbert & Berghoff LLP

(57) ABSTRACT

A system for dehydrogenating a C3 or C4 hydrocarbon feed stream containing a first and second layer of catalysts placed in the hydrocarbon feed stream, wherein the feed stream first passes through the first layer and then the second layer of catalysts and wherein the catalysts of the first layer contain from about 50 to about 90 percent by weight of an eta-alumina carrier, from about 10 to about 50 percent by weight of chromia and from about 0.1 to about 5 percent by weight of a zirconium compound and wherein the catalysts of the second layer of catalysts contain from about 50 to about 90 percent by weight of an eta-alumina carrier and from about 10 to about 50 percent by weight of chromia, without an added zirconium compound.

15 Claims, No Drawings

MULTI-LAYERED DEHYDROGENATION CATALYST SYSTEM AND PROCESS OF USE

CROSS REFERENCE TO RELATED APPLICATIONS

This application is a continuation-in-part application based on application Ser. No. 10/968,456, filed on Oct. 19, 2004, which application is a divisional application based on application Ser. No. 10/047,598 filed on Jan. 14, 2002, now abandoned.

BACKGROUND OF INVENTION

This invention relates to a multilayered catalyst system for the dehydrogenation of hydrocarbon feed streams, particularly C3 and C4 hydrocarbon feed streams, and processes for the manufacture and use of the catalyst system. This invention more specifically relates to a multi-layered catalyst system containing at least a first and a second layer of catalysts, wherein the first layer includes a chromia/alumina catalyst stabilized with a zirconium additive, wherein the alumina is eta alumina, and wherein the second layer includes a chromia/alumina catalyst, wherein the alumina is also eta alumina, but which does not contain a zirconium additive, which catalyst system is particularly useful for the dehydrogenation of an hydrocarbon feed stream, particularly a C3 and C4 alkane hydrocarbon feed stream, and processes for the manufacture and use of the catalyst system.

Alkane dehydrogenation is a recognized process for production of a variety of useful hydrocarbon products, such as isobutylene for conversion to MTBE, isooctane and alkylates to supplement and enrich gasolines and propylene for use in the polymer industry. There are several current catalytic processes useful for catalytic dehydrogenation of light alkanes, including Süd-Chemie CATOFIN® processes, the Linde/BASF process, UOP's OLEFLEX® process, Phillips' STAR™ process and the Snamprogetti-Yarsintee process. The catalysts that are used in these processes are manufactured from different types of catalytic materials. For example, the Süd-Chemie CATOFIN® processes utilize chromia-alumina catalysts.

Chromia-alumina dehydrogenation catalyst technology has been in use for over fifty years. In one example, GB 942,944 discloses a dehydrogenation catalyst for the dehydrogenation of aliphatic hydrocarbons having three to five carbon atoms. The catalyst disclosed was prepared by dehydrating an aluminum trihydrate composition comprising 60 to 100 percent beta alumina trihydrate, heating the resulting dehydrated alumina with steam to adjust its surface area to a range of 100 to 200 m²/g, depositing chromium oxide from about 10 to about 25 percent as $Cr_2O_3$ onto the resulting alumina carrier and steam treating the resulting catalyst at an elevated temperature.

The stability of a dehydrogenation catalyst plays an important role in the overall efficiency of the dehydrogenation process. Because of the high temperatures at which the catalytic dehydrogenation procedure is conducted, the life expectancy of the catalysts is often limited. Thus, improving the thermal stability of the catalysts translates into longer catalyst life, allowing for longer catalyst utilization and ultimately resulting in lower consumption of the catalysts during the dehydrogenation process.

One proposed method of stabilizing chromia-alumina dehydrogenation catalysts is by the addition of zirconia as disclosed in U.S. Pat. No. 2,374,404.

There are a number of different types of alumina that are available for use as the support for dehydrogenation catalysts. Conventionally, mid to high surface area gamma alumina has been the preferred choice as the carrier for such catalysts. In particular, gamma alumina has been preferred over eta alumina as the carrier for dehydrogenation catalysts.

This preference for gamma alumina over eta alumina for catalysts is not surprising because gamma alumina is generally perceived as having greater thermal stability than eta alumina. In fact, gamma alumina has become the standard alumina utilized for commercial catalysts. (The market has accepted this principle as gamma alumina is readily available in the market while eta alumina is sparsely available, if at all.)

Although dehydrogenation catalysts prepared from chromia-alumina catalysts have been extensively employed for many years, there are still opportunities for improvement, especially to improve the thermal stability. Even when these catalysts are stabilized by the addition of an additive, such as a zirconium or a silicon compound, they can still show limited stability because of the severity of the operating conditions, particularly at the high temperatures normally utilized during the dehydrogenation procedure.

Accordingly, it is an object of this invention to disclose an improved catalyst system for the dehydrogenation of hydrocarbon feed streams wherein the improved catalyst system includes at least two layers of different catalysts contained within the system through which the hydrocarbon feed stream passes in sequence.

These and other objects can be obtained by the catalyst systems, the processes for the preparation of the catalyst systems and the processes of use of the catalyst systems for the dehydrogenation of hydrocarbons which are disclosed by the present invention.

SUMMARY OF THE INVENTION

The present invention is a multilayer catalyst system for dehydrogenating a hydrocarbon feed stream comprising at least a first and a second layer of catalysts, wherein the first layer of catalysts through which the feed stream first passes comprises from about 50 to about 90 percent by weight of an eta alumina carrier, from about 10 to about 50 percent by weight of a chromium compound, and from about 0.1 to about 5 percent by weight of a zirconium compound added as a stabilizing material, and wherein the second layer of catalysts, through which the feed stream passes after passing though the first layer, comprises from about 50 to about 90 percent by weight of an eta alumina carrier and from about 10 to about 50 percent by weight of a chromium compound, wherein the catalysts do not include zirconium. Other stabilizers or additives may also be added to the composition of either catalyst, such as silicon materials, alkali metal compounds, or alkaline earth metal compounds, preferably potassium, sodium or cesium compounds. Each layer of catalysts may be loaded only with the desired catalyst or may further be mixed with inert materials, such as low surface area alpha-alumina.

The present invention is also a process for dehydrogenating a feed stream containing C3 and C4 hydrocarbons comprising preparing a first layer of catalysts, wherein the catalysts comprise from about 50 to about 90 percent by weight of an eta alumina carrier, from about 10 to about 50 percent by weight of a chromium compound, and from about 0.1 to about 5 percent by weight of a zirconium compound added as a stabilizing material; preparing a second layer of catalysts and placing said second layer of catalysts downstream from the first layer, wherein the catalysts of the second layer comprise from about 50 to about 90 percent by weight of an eta alumina carrier and from about 10 to about 50 percent by weight of a chromium compound, wherein the catalysts of the second layer do not include a zirconium compound; and passing the feed stream first through the first layer of catalysts and then through the second layer of catalysts. Each layer of catalysts may also include inert materials, such as alpha alumina.

The invention is also a process for the production of the dehydrogenation catalysts utilized in the multilayer catalyst system described above.

DETAILED DESCRIPTION OF THE INVENTION

The invention comprises a catalyst system for dehydrogenating a dehydrogenatable hydrocarbon feed stream, preferably a C3 and/or C4 alkane hydrocarbon feed stream, by passing said feed stream through at least a first and a second layer of catalysts, wherein the first layer, through which the feed stream preferably first passes, comprises from about 50 to about 90 percent of an eta alumina carrier, from about 10 to about 50 percent by weight of a chromium compound and from 0.1 to 5 percent by weight of a zirconium compound added to the catalyst as a stabilizing material, and the second layer of catalysts, through which the feed stream preferably passes after passing through the first layer, comprises from about 50 to about 90 percent of an eta alumina carrier and from about 10 to about 50 percent by weight of a chromium compound, wherein the second layer of catalysts does not include a zirconium compound. Other additives or stabilizing materials may be added to either or both of the catalysts of the first or second catalyst layers. In addition, quantities of inert materials are preferably blended with the active catalysts in each catalyst layer.

There are several types of aluminas that are available for use as the carrier material for each of the catalysts utilized in the two layers of the catalyst system. Conventionally, the alumina used for dehydrogenation catalysts has been a porous gamma-type alumina having a relatively high surface area of from about 120 $m^2/g$-300 $m^2/g$.

It has been surprisingly discovered that improved dehydrogenation catalysts are produced when the alumina utilized as a carrier for the catalysts of the catalyst system is predominantly eta alumina. Eta alumina carriers are conventionally produced by heating a bayerite form of aluminum trihydrate. Alternatively, the eta alumina may be acquired directly from alumina suppliers. However, because eta alumina has not been preferred for use as a carrier of catalysts, there is a limited market for this form of alumina. Most often eta alumina must be produced directly from its source material, i.e., by heating the bayerite form of aluminum trihydrate. The eta alumina carrier comprises from about 50 to about 90 percent, preferably about 70 to about 90 percent, and most preferably about 75 to about 85 percent, of the catalysts of each layer of the catalyst system, by weight.

Eta alumina is formed into shapes acceptable for use as the carrier of the catalysts of the catalyst system of the invention. For example, eta alumina pellets with a diameter of about ⅛ inch can be formed for use as the carrier by conventional procedures. These pellets are then dried and calcined by conventional procedures to produce a carrier with a surface area from about 100 $m^2/g$ to about 300 $m^2/g$, and preferably from about 120 $m^2/g$ to about 150 $m^2/g$.

A chromium compound is then added to the eta alumina carrier for the catalysts of both layers of the catalyst system. One method of adding the chromium compound requires dipping the eta alumina carrier into an aqueous solution of chromic acid, which is prepared by dissolving chromic oxide in water. Other chromium compounds can also be used as the source material for the chromium additive. The concentration of chromic oxide in solution must be sufficient to load the desired amount of chromia on the carrier. The impregnated eta alumina pellets are then dried and calcined using conventional procedures. The preferred loading of chromium oxide onto the eta alumina carrier is from about 10 to about 50 percent, preferably about 10 to about 30 percent and more preferably from about 15 to about 25 percent, by weight.

The above described process is the preferred process utilized for the preparation of the catalysts of the second layer for use in the system for dehydrogenating the C3 and/or C4 hydrocarbon feed stream of the invention. For this layer of catalysts, zirconium is not added to stabilize the catalysts. However, other additives may be added to the catalysts of this layer, such as silica, a lanthanum compound, alkali metal compounds, or alkaline earth metal compounds, such as potassium, sodium and cesium compounds. The concentration of the other additive(s) that may be added to the catalysts of this layer is in the range from about 0.1 to about 5 percent, by weight, and preferably from about 0.1 to about 1 percent, by weight.

In preparing the catalyst of the first layer of catalysts for use in the system for dehydrogenating hydrocarbon feed streams, particularly C3 and C4 hydrocarbon feed streams, the same eta-alumina carrier, as discussed above, is prepared. In addition, the chromium compound, as discussed above, in the same proportions as discussed above, is added to the eta-alumina carrier. However, in contrast to the catalysts of the second layer, a stabilizing additive, preferably zirconia, is added to the chromia-eta alumina catalysts discussed above to form the catalysts of the first layer of the catalyst system.

To form these stabilized catalysts, the chromia-eta alumina catalysts discussed above are preferably impregnated with a zirconium solution formed from a zirconium salt, such as zirconyl nitrate. Preferably, the concentration of the solution of the zirconium salt is sufficient to produce a loading on the chromia-eta alumina catalyst from about 0.1 percent to about 5 percent by weight, preferably from 0.1 percent to 1 percent by weight. As a preferred alternative process to the zirconium compound being separately added to the chromia-eta alumina catalysts, the zirconium compound can be coimpregnated with the chromium compound on the eta alumina carrier. In this process, a zirconium salt, preferably zirconyl carbonate at the appropriate concentration, is dissolved in chromic acid and the two compounds are then coimpregnated into the eta alumina carrier.

After impregnation the catalysts of the first layer are dried and then calcined at conventional temperatures to form the catalysts for use in the first layer of the catalyst system.

Other additives may also be added to the catalysts of the first layer, such as silica, lanthanum compounds, alkali metal compounds or alkaline earth metal compounds, such as potassium, sodium and cesium compounds. The concentration of the additional additive(s) on the catalysts that may be added is in the range of about 0.1 to about 5.0 percent, by weight, and preferably from about 0.1 to about 1.0 percent, by weight.

The surface area of both catalysts is preferably from about 60 $m^2/g$ to about 120 $m^2/g$.

It has been surprisingly discovered that a dehydrogenation catalyst system made utilizing eta-alumina as the carrier for the catalysts of both catalyst layers provides improved performance over prior art dehydrogenating catalyst systems which utilize other carriers, particularly gamma alumina. This is especially surprising as gamma alumina has become the standard carrier used for dehydrogenation catalysts of this type. It has also been surprisingly discovered that there is a synergistic relationship between the use of the zirconium additive and the eta-alumina carrier in the catalyst of the first layer, which produces surprisingly large improvements in the performance and stability of the catalysts of the first layer over conventional catalysts produced from gamma alumina. In particular, it has been discovered that the performance of aged catalysts of the invention in a conventional dehydrogenation reaction are surprisingly better than conventional dehydrogenation catalysts produced utilizing gamma alumina carriers. In addition, there is an improvement in the selectivity of the catalysts of the invention and also an improvement in yield. Further, the catalysts of the invention are also more stable during the dehydrogenation reaction than conventional gamma alumina based catalysts.

The present invention is also a method of dehydrogenating a hydrocarbon feed stream, particularly a feed stream containing C3 to C4 hydrocarbons, using the catalysts arranged in two layers of catalysts of the invention. According to one embodiment of the invention, C3 and C4 aliphatic hydrocarbons contact the first and second layers of catalysts of the invention, as described above, in a dehydrogenation zone maintained at dehydrogenation conditions. The contacting step may be accomplished in a fixed catalyst bed system or in a batch type operation. However the fixed bed system is preferred. In this fixed bed system, the preferred hydrocarbon feed stream is preheated to the desired reaction temperature and then passed into the dehydrogenation zone containing the fixed bed with at least the two catalyst layers. While the hydrocarbon feed stream may be contacted with a catalyst bed in an upward, downward or radial flow pattern, the arrangement of the catalysts within that catalyst bed is important. The hydrocarbon feed stream should first encounter the first layer of catalysts, comprising the first catalysts described above, which is comprised at least of eta-alumina, chromia and zirconia as a stabilizing material. Additional additives may be added to the catalysts, as described above, including alkali metal compounds or alkaline earth metal compounds, such as potassium, sodium or cesium compounds.

The first layer of the catalyst bed is preferably formed by combining the eta alumina/chromia/zirconia catalysts discussed above with inert materials, if used. The inert materials comprise a material which neither promotes catalytic reactions nor interferes with the desired catalytic reaction that occurs within the reactor. In a preferred embodiment the inert material comprises an alpha alumina or a ceramic material in a size similar to that of the active catalyst material. Different sized inert materials can be utilized as long as there is not a significant movement of either the catalysts or the inert material within the catalyst bed after loading. Preferably, the inert material comprises from about 1 to about 70 percent, by volume, of this layer of the catalyst bed, more preferably from about 10 to about 70 percent of the layer, and most preferably from about 40 to about 60 percent of the layer, by volume.

Following preparation of the first layer of the catalyst material, the second layer of the catalyst material is prepared, wherein the catalyst material preferably comprises the chromia/eta-alumina catalyst described above, which does not include a zirconium compound. However, other additives may, and preferably are added to this second catalyst material including alkali materials or alkaline earth metal materials, such as sodium, potassium or cesium compounds. In addition, as described above for the first catalyst layer, preferably from about 1 to about 70 percent, more preferably from about 10 to about 70 percent of this catalyst layer, and most preferably from about 40 to about 60 percent of this catalyst layer, by volume, is comprised of the inert material described above.

In one embodiment the first layer active catalyst material, which contains zirconium as an additive, comprises from about 5 to about 90 percent of the total active catalytic material, by weight in the catalyst system. In a preferred embodiment, the first catalyst material comprises from about 10 to about 70 percent of the total active catalyst material, by weight, and in a most preferred embodiment from about 15 to about 75 percent of the total active catalyst material, by weight in the catalyst system.

Preferably, the two layers are located one above the other with the first layer of catalysts located in the top of the catalyst bed and the second layer located in the bottom of the catalyst bed.

Additional layers of either or both types of catalysts or layers solely formed of inert materials may be added to the catalyst bed as desired.

Typical dehydrogenation conditions include a temperature from about 400° to about 900° C., a pressure from 0.01 to 10 atmospheres and a liquid hourly space velocity (LHSV) from about 0.1 up to about 100 HR.$^{-1}$. Generally for aliphatic hydrocarbons, the lower the molecular weight, the higher the temperature that is required for comparable conversions. Thus, as the above-referenced hydrocarbon feed stream is preferably C3 and C4 hydrocarbons, the dehydrogenation temperatures utilized should be in the range from about 500° C. to about 800° C., preferably from about 550° C. to about 750° C. The pressure in the dehydrogenation zone is maintained as low as practical consistent with the equipment limitations to maximize the chemical equilibrium advantages.

The hydrocarbon feed stream exiting from the dehydrogenation zone generally contains unconverted hydrocarbons, hydrogen and the products of the dehydrogenation reaction. This feed stream is typically cooled and passed to a hydrogen separation zone to separate a hydrogen rich vapor phase from a hydrocarbon rich liquid phase. Generally the hydrocarbon rich liquid phase is further separated by means of a suitable selective adsorbent, selective solvent, selective reaction or reactions or by means of a suitable fractionation scheme. Unconverted dehydrogenatable hydrocarbons are recovered and may be recycled through the dehydrogenation zone. Products of the dehydrogenation reaction are recovered as final products or intermediate products for the preparation of other compounds.

To be commercially successful a dehydrogenation catalyst should exhibit three characteristics: high activity, high selectivity and good stability. Activity is a measure of the catalyst's ability to convert reactants into products under a specified set of reaction conditions, such as a specified temperature, pressure, contact time and concentration of diluent, such as hydrogen, if any. For dehydrogenation catalyst activity, the conversion or disappearance of paraffins relative to the amount of paraffins originally in the feed stream is measured.

Selectivity is a measure of the catalyst's ability to convert reactants into the desired product or products relative to the amount of reactants converted. For catalyst selectivity, the amount of olefins in the product, in mole percent, relative to the total moles of the parrafins converted are measured.

Stability is a measure of the rate of change with time on stream of the activity and selectivity parameters of the catalysts. Smaller rates of change imply a more stable catalyst.

According to the unique composition of the catalyst bed of the present invention, significant differences have been discovered when comparing the performance of the above-referenced unique layered catalyst system with a conventional dehydrogenation catalyst bed. When reactions are compared, significant improvements are shown in activity, which improvements occurred quickly and continued for an extended period of time. The increase in activity is as much as 100 percent over a catalyst bed comprising only a conventional chromia/alumina catalyst without zirconium. While improved performance was noted when the catalyst beds were operated at the same temperature, the layered catalyst system of the invention also maintained at least the same conversion as the prior art catalysts when the temperature of the reaction using the layered catalyst was reduced, even by as much as 10° C. This results in a significant savings because of the high temperatures at which the reactors must be heated during the reaction.

It is anticipated that this same level of improvement cannot be achieved merely by using the first catalysts containing zirconium of the first layer alone throughout the entire catalyst bed because there are different requirements of catalyst stability in each portion of the catalyst bed. Without being bound to any particular theory, a possible explanation for the unexpected improvement is that for best performance, the catalyst of the bottom layer requires a short period of aging. This aging provides an improvement of the catalyst properties for operation in a high olefins concentration environment. As the bottom layer of the bed operates at about 50-100° C. lower temperature than the top layer, the catalysts at the bottom age at a much slower rate than the catalysts at the top. At these conditions the stabilized catalyst with zirconium is too stable and does not allow changes in the catalysts' properties to occur which result in improved performance. The inventors have discovered that surprising improvements are achieved when the two layers of catalysts are used in the catalyst system in combination and when the percentage of the catalysts containing the zirconium is maintained within the ranges described herein. This improvement in performance is certainly a surprising improvement and not anticipated merely by the addition of zirconium to a portion of the catalysts as a stabilizing material.

It will be apparent from the foregoing that while particular forms of the invention have been illustrated, various modifications can be made without departing from the scope of the invention. Accordingly, this description is not intended to limit the invention.

The invention claimed is:

1. A catalyst system for dehydrogenating an alkane hydrocarbon feed stream and having improved selectivity and yield, the catalyst system comprising:
    a first catalyst comprising about 50 to about 90 percent by weight of an eta alumina carrier, about 10 to about 50 percent by weight of a chromium compound, and about 0.1 to about 5 percent by weight of a zirconium compound, wherein the chromium compound and the zirconium compound are impregnated on the eta alumina and the zirconium compound functions to stabilize the chromium compound; and
    a second catalyst comprising about 50 to about 90 percent by weight of eta alumina carrier and about 10 to about 50 percent by weight of a chromium compound, and wherein the second catalyst does not include a zirconium compound;
    wherein a plurality of the first catalyst forms a first catalyst layer of the catalyst system and a plurality of the second catalyst forms a second catalyst layer of the catalyst system that is downstream of the first catalyst layer relative to the flow of the feed stream over the first and second catalyst layers such that the hydrocarbon feed stream first contacts the first catalyst layer and then contacts the second catalyst layer to produce a dehydrogenated unsaturated alkene or alkadiene hydrocarbon product, and
    the first catalyst layer comprises about 5 to about 90 weight percent of the catalyst system.

2. The catalyst system of claim 1 wherein the hydrocarbon feed stream comprises $C_3$ hydrocarbons, $C_4$ hydrocarbons, and mixtures thereof.

3. The catalyst system of claim 1 wherein the first catalyst layer comprises about 15 to about 75 weight percent of the catalyst system.

4. The catalyst system of claim 1 wherein eta alumina as a carrier comprises about 70 to about 90 percent of each of the first catalyst and the second catalyst, by weight.

5. The catalyst system of claim 1 wherein the chromium compound comprises about 10 to about 30 percent of each of the first catalyst and the second catalyst, by weight.

6. The catalyst system of claim 1 wherein the first catalyst further comprises an alkali metal additive or an alkaline metal additive selected from the group consisting of potassium, sodium and cesium compounds and mixtures thereof.

7. The catalyst system of claim 1 wherein the second catalyst further comprises an alkali metal additive or an alkaline metal additive selected from the group consisting of potassium, sodium and cesium compounds and mixtures thereof.

8. The catalyst system of claim 1 wherein the first catalyst layer further comprises about 1 to about 70 percent of an inert material, by volume.

9. The catalyst system of claim 1 wherein the second catalyst layer further comprises about 1 to about 70 percent of an inert material, by volume.

10. The catalyst system of claim 1 wherein the first catalyst layer further comprises from about 40 to about 60 percent of an inert material, by volume.

11. The catalyst system of claim 1 wherein the second catalyst layer further comprises from about 40 to about 60 percent of an inert material, by volume.

12. A process for dehydrogenating a $C_3$ and $C_4$ hydrocarbon feed stream and having improved selectivity and yield, the process comprising;
    preparing a first catalyst, wherein the first catalyst comprises about 50 to about 90 percent by weight of eta alumina, about 10 to about 50 percent by weight of a chromium compound, and about 0.1 to about 5 percent by weight of a zirconium compound, wherein the chromium compound and the zirconium compound are impregnated on the eta alumina and the zirconium compound functions to stabilize the chromium compound,
    preparing a second catalyst, wherein the second catalyst comprises about 50 to about 90 percent by weight of eta alumina, about 10 to about 50 percent by weight of a chromium compound and does not include a zirconium compound,
    wherein a plurality of the first catalyst forms a first catalyst layer of the catalyst system and a plurality of the second catalyst forms a second catalyst layer of the catalyst system that is downstream of the first catalyst layer relative to the flow of the feed stream over the first and second catalyst layers; and passing the feed stream through the first catalyst layer and the second catalyst layer such that the hydrocarbon feed stream first contacts the first catalyst layer and then contacts the second catalyst layer to produce a dehydrogenated $C_3$ and $C_4$ hydrocarbon product, wherein the first catalyst layer comprises about 5 to about 90 weight percent of the catalyst system.

13. The process of claim 12 wherein the first catalyst layer containing zirconium comprises from about 15 to about 75 weight percent of the catalyst system.

14. The process of claim 12 wherein the first catalyst layer further comprises from about 1 to about 70 percent by volume of an inert material.

15. The process of claim 12 wherein the second catalyst layer further comprises from about 1 to about 70 percent by volume of an inert material.

* * * * *